US00PP27031P3

(12) United States Plant Patent
Maillard et al.

(10) Patent No.: US PP27,031 P3
(45) Date of Patent: Aug. 9, 2016

(54) APRICOT TREE NAMED 'APRIREVE'

(50) Latin Name: ***Prunus armeniaca* L.**
Varietal Denomination: APRIREVE

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 169 days.

(21) Appl. No.: 14/120,775

(22) Filed: Jun. 26, 2014

(65) Prior Publication Data

US 2015/0156937 P1 Jun. 4, 2015

(30) Foreign Application Priority Data

Dec. 2, 2013 (QZ) ..... PBR 2013/3065

(51) Int. Cl.
*A01H 5/08* (2006.01)

(52) U.S. Cl.
USPC ..... Plt./186

(58) Field of Classification Search
USPC ..... Plt./186
CPC ..... A01H 5/0843
See application file for complete search history.

*Primary Examiner* — Kent L Bell
(74) *Attorney, Agent, or Firm* — Westerman, Hattori, Daniels & Adrian, LLP

(57) ABSTRACT

A new and distinct variety of apricot tree, denominated 'APRIREVE', characterized by its self-fertility and no susceptibility to pests and diseases and by fruits of very good firmness, of very long shelf life without alteration after harvesting, and with an orange flesh of high eating quality, aromatic and with a high level of sugar, and with an attractive luminous orange red skin on a yellow orange background.

2 Drawing Sheets

Botanical classification: *Prunus armeniaca* L.

Variety denomination: 'APRIREVE'.

This application claims priority of Community plant variety right No. 2013/3065 filed on Dec. 2, 2013 (Dec. 2, 2013), which is hereby incorporated by reference in its entirety.

BACKGROUND OF THE NEW VARIETY

The present invention relates to a new and distinct variety of apricot tree, *Prunus armeniaca* L., which has been given the variety denomination 'APRIREVE'. This new tree produces fruit with a long shelf life without alteration after harvesting, very good eating quality, and orange flesh fruit for fresh market in early June in the Pyrénées-Orientales departement, France.

Contrast is made to 'ASFCOT0404', also named 'APRIQUEEN' (U.S. Plant Pat. No. 21,138), an apricot tree, for reliable description. Contrast is also made to the parent varieties.

'APRIREVE' is a promising candidate for commercial success in that it has very attractive fruits with long shelf life without alteration after harvesting. This new variety results from our plant-breeding program aimed at obtaining apricot trees producing fruits of sweet and very aromatic taste, with an attractive yellow orange skin covered by an appealing orange red blush. One of our main concerns is also the production of new varieties producing fruits having a long shelf life after harvesting, in order to facilitate long distance shipping. Our final purpose is the production of a range of new apricot tree varieties differing by their time of maturity, while producing fruits of very similar characteristics, in order to provide markets with almost indistinguishable fruits during the whole period of production of apricot.

ORIGIN OF THE VARIETY

The 'APRIREVE' apricot tree originated in a cultivated area of the south of France, in the Pyrénées-Orientales departement, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'APRIREVE' variety was propagated by grafting on a 'FRANC INRA® MONTCLAR' (non patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

The 'APRIREVE' variety results from a pollinated cross between the 'APRIROME' apricot tree, also known as 'ASFCOT0406' (U.S. Plant Pat. No. 21,136), which was used as the seed parent, and the 'APRIBANG' variety, also known as 'ASFCOT0405' (U.S. Plant Pat. No. 21,137) apricot tree, which was used as the pollen parent.

SUMMARY OF THE VARIETY

The new and distinct variety of apricot tree blooms generally during March in the Pyrénées-Orientales departement, France. More particularly, the blooming period generally starts between March $5^{th}$ and March $17^{th}$. However, it was observed that its early date of blooming seems to be highly dependant on climatic conditions.

The first fruit of 'APRIREVE' apricot tree ripens during June, generally about 4 days earlier than 'ASFCOT0404' (U.S. Plant Pat. No. 21,138). However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
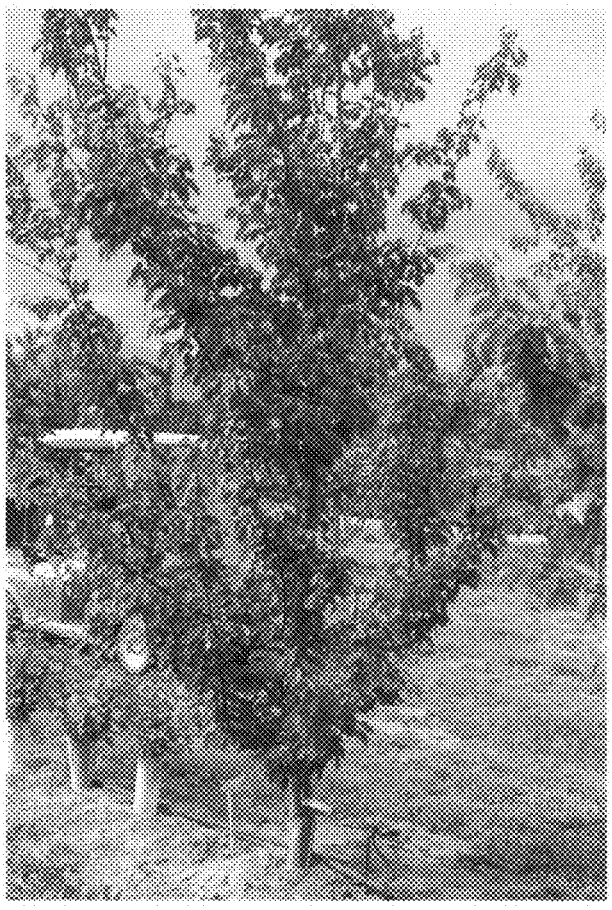
FIG. 1 is a color photograph, which shows a view of an apricot tree of the new variety in orchard, bearing fruits.
Figure 2:
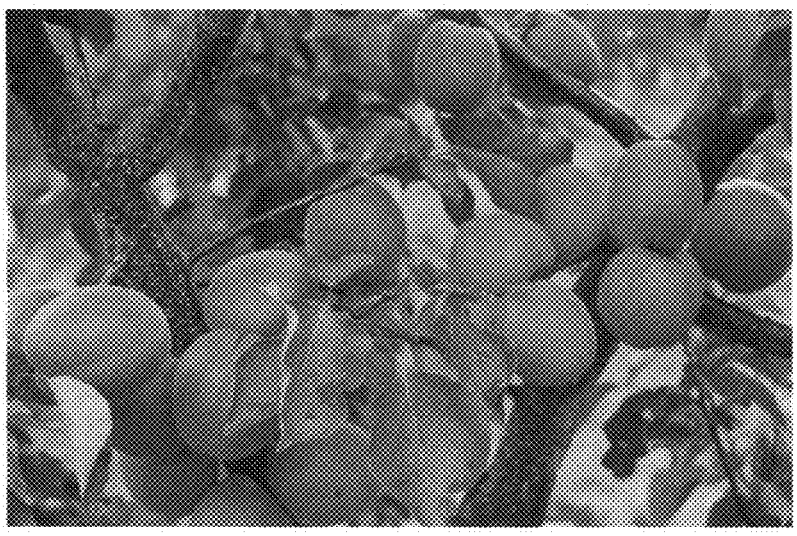
FIG. 2 is a color photograph, which shows a closest view of branches of the new variety in orchard, bearing fruits.
Figure 3:
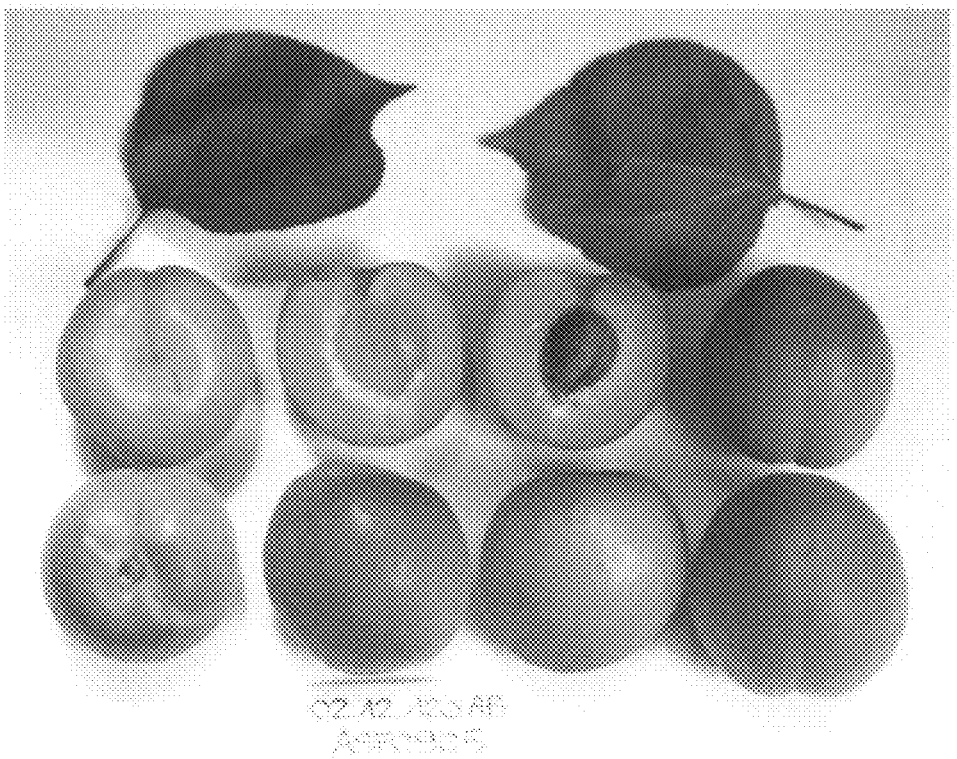
FIG. 3 is a color photograph, which shows six whole fruits and leaves of the new variety, and a seventh fruit, cut in half, with the stone left in one of the halves for depicting the fruit flesh the stone and the stone cavity of the new variety.
Figure 4:
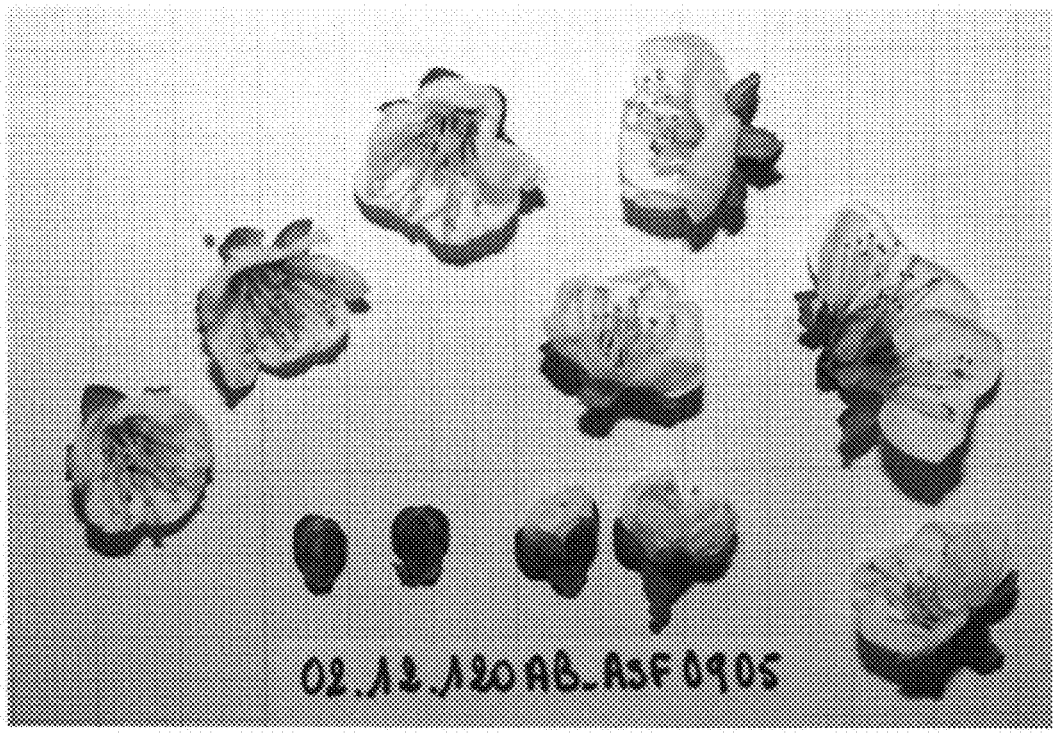
FIG. 4 is a color photograph with reverse and side views of flowers of the new variety, and, with petals removed, reproductive organs of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'APRIREVE' is high, due to fruit very long shelf life without alteration after harvesting.

Trees are vigorous and medium stature in a naturally semi-upright out aspect. The time of beginning of flowering is considered medium; flowering begins during the month of March. The flower petals are small and colored in white or in a extremely pale pink. Leaf glands are present and round. Time of maturity for consumption is considered early, namely during the month of June. The fruit flesh is considered orange. The fruit skin is medium thick and colored with an orange red blush on a yellow orange background. The stone is medium size. Fruit taste is very aromatic and with a high level of sugar.

Compared to 'ASFCOT0404' (U.S. Plant Pat. No. 21,138) apricot tree, 'APRIREVE' variety ripens approximately 4 days earlier, as set forth above. 'APRIREVE' variety produces very attractive large fruits, with an orange red coloration, covering between 60 and 70% of the fruit skin, on an orange yellow background. In comparison, 'ASFCOT0404' apricot tree produces fruits with a dark orange coloration covering 30 to 40% of the skin, on an orange background. 'APRIREVE' fruits show a good behaviour and a long shelf life both on the tree after growth completion and after harvesting. The time of maturity of the new variety is also interesting, because it ripens just a few days before 'ASFCOT0404' variety.

Compared to its male parent 'ASFCOT0405' (U.S. Plant Pat. No. 21,137) apricot tree, the new variety 'APRIREVE' blooms slightly earlier. More particularly, 'APRIREVE' blooms 2 to 3 days before 'ASFCOT0405'. The new variety 'APRIREVE' also ripens earlier than 'ASFCOT0405', generally about 10 days earlier. The fruits of the new variety 'APRIREVE' are more colourful. They show a red orange color covering 60 to 70% of the skin, on an orange yellow background. In comparison, the fruits of 'ASFCOT0405' are colored with a red blush covering 30 to 50% of the skin, on a luminous orange background. The fruit form of 'APRIREVE' is considered slightly oblong, whereas the fruits of 'ASFCOT0405' are round-shaped.

Compared to its female parent 'ASFCOT0406' (U.S. Plant Pat. No. 21,136) apricot tree, the new variety 'APRIREVE' blooms slightly earlier. More particularly, 'APRIREVE' blooms 4 to 5 days before 'ASFCOT0406'. The new variety 'APRIREVE' also ripens earlier than 'ASFCOT0406', generally about 12 days earlier. The fruits of the new variety 'APRIREVE' are more colourful. They show a red orange color covering 60 to 70% of the skin, on an orange yellow background. In comparison, the fruits of 'ASFCOT0406' are colored with a very luminous red blush covering 50 to 60% of the skin, on a shiny orange background. The fruit form of 'APRIREVE' is considered slightly oblong, whereas the fruits of 'ASFCOT0406' are round and conic-shaped.

DETAILED DESCRIPTION

Referring more specifically to the pomological details of this new and distinct variety of apricot tree, the following was observed on trees during the 2011 and 2012 growing seasons under the ecological conditions prevailing at the orchards located near the town of Elne, Pyrénées-Orientales departement, France. All observations have been done on rootstock cultivars. Used rootstocks were 'FRANC INRA® MONTCLAR' (non patented) trees. All major color code designations are by reference to The R.H.S. Color Chart (Fourth Edition) provided by The Royal Horticultural Society of Great Britain.

Tree:

*Size*.—Generally. — Considered medium as compared to other common commercial apricot cultivars. Trees reach about 250 cm during the first growing season. Trees were pruned during each following season to a height of approximately 250 cm and to a diameter of 200 cm.

*Spread*.—Approximately 200 cm. The whole orchard was oriented to a central leader organization, with tree lines spaced of 4.0 meters and trees spaced of 1.0 meter in a same tree line.

*Vigor*.—Considered medium to strong vigorous. Current season shoots growth could reach 100 cm. During the first year of growth, trees growth reaches 250 cm. In the second and following seasons, the size of trees is reduced to 250 cm by pruning. However, these characteristics are dependant on soils fertility, cultural practices, and prevailing climatic conditions.

*Productivity*.—Very Productive and regular. Fruit set is spaced by thinning to develop the remaining fruit into the desired market sized fruit. Because of the fruit size, the new variety only requires a medium thinning for the tree valorisation. Thinning was necessary every year during the years of observation. The number of the fruit set varies with the prevailing climatic conditions and cultural practices employed during the bloom period, and is therefore not distinctive of the present variety.

*Bearer*.—Very regular. No alternate bearing was observed.

*Form*.—The 'APRIREVE' variety has a naturally semi-upright shape.

*Density*.—Considered highly dense, in order to obtain and observe fruits more quickly.

*Fertility*.—The 'APRIREVE' variety is considered autofertile. A genetic analysis has been done during year 2013 in order to confirm the autofertile characteristic of 'APRIREVE' variety.

*Hardiness*.—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. The tree also seems to have a good resistance to frosty springtime weather.

Trunk:

*Diameter*.—Approximately between 8.0 cm and 9.0 cm in diameter when measured at a distance of approximately 30 cm above the soil level.

*Bark texture*.—Considered smooth to rough when numerous lenticels are present.

*Bark coloration*.—The bark has mostly an orange brown (RHS Greyed Orange 166A) coloration or a brown color (RHS Brown 200B).

*Lenticels*.—Lenticel color. — A light orange color (RHS Orange White 159C) or a light grey color (RHS Greyed Yellow 161D). Density. — Numerous lenticels are present, approximately 5 to 6 lenticels per $cm^2$. Size. — Lenticels are approximately 1.5 to 2.0 millimeters in width and 3.0 to 4.0 millimeters long.

Branches:

*Size*.—Current season shoots are considered medium for the variety. Mature branches are considered medium to large for the variety.

*Diameter*.—Average as compared to other apricot varieties. The current season shoots have a diameter from 4.0 to 6.0 millimeters, and mature branches have a diameter from 28.0 to 36.0 millimeters.

*Surface texture*.—Current season shoots have a smooth texture. Mature branches are medium rough. Roughness increases with trees age.

*Crotch angles*.—The crotch angles are generally between 45 and 55 degrees from the trunk axis. At maturity, the crotch angle increases with fruits weight. This particular characteristic is not considered distinctive of the variety, however.

*Internode length*.—Generally between 20.0 and 28.0 millimeters.

*Color of mature branches*.—Brown (RHS Brown 200 B to RHS Brown 200 C).

*Color of current season's shoots*.—Considered orange brown (RHS Greyed Orange 166 A). The current season's shoots color evolves and turns to mature branches color when aging.

*Vigor*.—Considered vigorous.

*Lenticels*.—Density. — Numerous lenticels are present, just as on the trunk, especially on mature branches. Size. — Considered slightly smaller than trunk's lenticels, they are approximately 1.0 millimeter wide and 2.0 to 3.0 millimeters long. Color. — Similar to the color of the trunk's lenticels, namely a light orange color (RHS Orange White 159C) or a light grey color (RHS Greyed Yellow 161 D).

Leaves:

*Size*.—Considered medium for the species. The ratio length/width is equal to 1.22.

*Leaf length*.—Approximately 69.0 to 88.0 millimeters (average 77.9 millimeters).

*Leaf width*.—Approximately 58.0 to 77.0 millimeters (average 64.0 millimeters).

*Leaf form in cross section*.—Concave.

*Leaf form*.—Circular and cordate.

*Leaf tip form*.—Acuminate.

*Leaf base form*.—Generally round.

*Leaf margins*.—Considered dentate.

*Thickness*.—Medium.

*Upper surface texture*.—Smooth.

*Lower surface texture*.—Smooth.

*Leaf colour*.—Upper leaf surface. — Green (RHS Green Group 137 A to RHS Green Group 137 B). Lower surface. — A lighter green (RHS Yellow Green Group 146 A to RHS Yellow Green Group 146 B) than the upper leaf surface color.

*Leaf venation*.—Pinnately veined.

*Mid-vein*.—Thickness: Approximately 2.0 millimeters when measured at the base of the leaf. Color: Red purple (RHS Red Purple Group 59B). Other veins color: Light green (RHS Yellow Green 145 A to RHS Yellow Green 145 B). Uniformity: Leaves are of medium size and generally found alone. No stipules are generally found.

*Leaf petioles*.—Size. — Generally medium to long. Length. — Between 27.0 and 38.0 millimeters. Diameter. — Approximately 2.0 millimeters. Surface. — Generally slightly ribbed.

*Petioles colour*.—Upper petiole surface. — Depending on climatic conditions and sunlight exposure, the anthocyanic coloration on petiole's upper surface is generally considered purple red (RHS Red Purple 59 A to RHS Red Purple 59 B).

*Leaf glands*.—Size. — Considered small. Length. — Approximately 0.5 millimeter. Width. — Approximately 0.5 millimeter. Number. — Between 2 and 3 glands per leaf. Type. — Circular. Margins. — Smooth and regular. Position. — Alternate between upper portion of petiole and lower portion of leaf blade. Color. — Generally grey orange (RHS Greyed Orange Group 165 A).

*Leaf stipules*.—Generally. — No leaf stipules were observed.

Flowers:

*Flower buds*.—Generally. — At pre-floral stage of development, the floral buds are conic in form with a very rounded tip (ball shaped). Their form is evolving until blooming, with variables dimensions. Just before blooming, floral buds are approximately 10.0 millimeters wide and approximately 14.0 millimeters long. Generally, a bud is found alone or in group of two or three buds. Color. — This characteristic is dependent upon the proximity to bloom. At pre-floral stage of development, the bottom of the flowers buds, formed by the sepals, is of purple-brown color (RHS Greyed Purple 184 B to RHS Greyed Purple 184 C); the corolla, formed by the petals, is generally of white color with a very slightly pink pigmentation (RHS White Group N 155 B to RHS White Group N 155 C or RHS Greyed Purple Group 186 D). The petal color generally evolves until the end of the blooming period, becoming whiter.

*Hardiness*.—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—During March.

*First bloom*.—The first bloom was observed on Mar. 5, 2011.

*Petal fall*.—Mar. 14, 2011.

*Blooming time*.—Considered medium season in relative comparison to other commercial apricot cultivars grown in the Pyrénées-Orientales departement, France. Thus, the first blooming time was from Mar. 5 to Mar. 14, 2011. The next observed blooming periods were from Mar. 17 to Mar. 23, 2012, from Mar. 17 to Apr. 2, 2013 and from Mar. 7 to Mar. 16, 2014.

*Flower type*.—The variety is considered to have a showy type of flower.

*Duration of bloom*.—Approximately between 7 and 17 days.

*Flower size*.—Flower diameter at full bloom is approximately 16.0 to 23.0 millimeters.

*Bloom quantity*.—Considered abundant, flowers are generally found in bunches.

*Flower bud frequency*.—Generally 1 flower bud or several flower buds per groups of 2 to 3.

*Petal size*.—Generally. — Small. Length. — Generally between 12.0 and 14.0 millimeters. Width. — Generally between 13.0 and 15.0 millimeters.

*Petal form*.—Round-shaped.

*Petal count*.—Generally 5, overlapping with sepals.

*Petal texture*.—Smooth, soft and glabrous to very slightly wrinkled.

*Petal color*.—Both surfaces of petals are colored with a white (RHS White Group N 155 B to RHS White Group N 155 C) to a very light pink (RHS Greyed Purple Group 186 D) color.

*Fragrance*.—Pronounced.

*Petal claw*.—Narrow and generally colored like petal color (RHS White Group N 155 B to RHS White Group N 155 C or RHS Greyed Purple Group 186 D).

*Petal margins form*.—Slightly wavy especially near the base.

*Petal base*.—Narrow at point of attachment.

*Petal apex*.—Wide-dome shaped.

*Petal peduncle*.—Length. — Approximately 3.0 to 5.0 millimeters. Diameter. — Approximately 2.0 millimeters. Color. — Generally yellow green (RHS Yellow Green 145 B to RHS Yellow Green C) and covered with small overlapping scales colored purple brown (RHS Greyed Red 178 A to RHS Greyed Red 178 B) or orange brown (RHS Greyed Orange 175 A to RHS Greyed Orange 175 B).

*Sepals*.—Generally. — Star shaped around the corolla base. Length. — Approximately between 5.0 and 6.0 millimeters. Width. — Approximately between 4.0 and 6.0 millimeters. Sepal count. — Generally 5, sometimes 6. Form. — Triangular, with a slightly pointed apex. Color. — Generally, both surfaces of sepals are colored with a purple brown (RHS Greyed Purple 184 B to RHS Greyed Purple 184 C or RHS Greyed Purple 185 B to RHS Greyed Purple 185 C) color. Texture. — Smooth.

*Stamens*.—Average number of stamens per flower. — Between 27 and 33. Size. — Approximately between 8.0 and 11.0 millimeters in length, generally smaller or equal to pistil's length. Generally, stamens are shorter or equal to petals. Color. — White (RHS White Group N 155 B to RHS White Group N 155 C).

*Anthers*.—Size. — Generally small. Color. — Orange Yellow (RHS Yellow Orange 16 A to RHS Yellow Orange 16 B), which may evolve with maturity.

*Pistil*.—Number. — Usually 1. Length. — Approximately 16.0 to 19.0 millimeters including the ovary. The pistil's length is equal or higher than stamen's length. Generally stigmas are at the same level as anthers or above. Color. — Considered white (RHS White Group 155 C) or very pale green (RHS Yellow Green 145 D).

*Pollen*.—Pollen production. — Pollen production is considered good. The fertility has been check through a DNA lab in 2013 and confirmed the self-fertility of the variety. Color. — Orange yellow color (RHS Yellow Orange 16 A to RHS Yellow Orange 16 B).

*Calyx*.—Internal surface texture. — Smooth and glabrous. Color. — The inner surface of the calyx is considered orange (RHS Yellow Orange 22 A or RHS Yellow Orange 24 A or RHS Yellow Orange 25 A) whereas the outer surface is purple (RHS Greyed Purple 185 B to RHS Greyed Purple 185 C) becoming slightly lighter near calyx base and green near the peduncle.

Fruit:

*Maturity*.—Considered semi-early. Generally, fruits become mature during June.

*Date of first picking*.—Jun. 14, 2009.

*Date of last picking*.—The date of harvest varies slightly with the prevailing climatic conditions. The 'APRIREVE' variety has a semi early date of picking and a grouped maturity. The maturity is usually grouped within 3 to 7 days and the harvest is generally performed in two runs. e first picking was carry on from Jun. 14 to Jun. 16, 2009. The next picking times were from Jun. 20 to Jun. 24, 2010, then from May 31 to Jun. 4, 2011, then from Jun. 11 to Jun. 17, 2012 and from Jun. 23 to Jun. 29, 2013.

*Size*.—Generally. — Considered large. Length. — Approximately 49.0 to 55.0 millimeters. Width. — Approximately 47.0 to 52.0 millimeters. Thickness. — Approximately 45.0 to 51.0 millimeters.

*Typical weight*.—Generally between 63.0 and 90 grams. The average weight is about 69.5 grams. This characteristic is high dependent upon the prevailing cultural practices, and therefore is not particularly distinctive of the variety.

*Fruit form*.—Generally. — Round and slightly oblong near the apex and at the fruit base. The fruit is considered to be symmetrical.

*Suture*.—Generally. — Moderately marked, extending from the base to the apex. Color. — The suture has generally a color similar to the whole fruit color. The suture is colored with an orange red color (RHS Orange Red 34 A).

*Ventral surface*.—Form. — Round.

*Apex*.—Flat.

*Base*.—Straight to slightly retuse.

*Stem cavity*.—Shallow. Average depth of the stem cavity is about 9.0 millimeters. Average width is about 7.5 millimeters.

*Stem*.—Size. — Generally large. Stem length is about 7.5 millimeters. Stem diameter is about 4.0 millimeters. Color. — Stem color is generally green (RHS Yellow Green 145 A).

*Fruit skin*.—Thickness. — Considered medium to strong, adherent and resistant. Texture. — Slightly rough. Pubescence. — Present but very light, almost non-existent. Tendency to crack. — None observed.

*Color*.—Blush color. — This blush color is orange red (RHS Orange Red 34 A). The orange red blush covers between 60 and 70% of the fruit skin surface for fruits that are exposed to sunlight. The percentage of the blush on the fruit skin surface can vary, and is generally dependant upon the prevailing conditions under which the fruit was grown. Ground color. — The ground color covers 30 to 40% of the fruit skin surface, and is considered orange yellow (RHS Yellow Orange 22 A). Adherence to flesh. — Adherent. Taste. — Moderately acid.

*Flesh*.—Ripens. — The maturing of the fruit is uniform. Texture. — Fine and firm. Very melting and juicy at end of maturity. Fibers. — Generally none observed. Aroma. — Very present, pronounced. Firmness. — Firm. Holds firmness over the time. Eating quality. — Considered very good and with a high level of sugars. Flavor. — Considered very good. Semi sweet and with a good balance between sugar and acidity. Very aromatic. Juice. — Very juicy. The juiciness increases with maturity. Brix. — Generally superior to 16.0 degrees, between 16.0 and 21.0 degrees. The average Brix is about 17.8 degrees. This characteristic varies slightly with the number of fruits per tree, prevailing cultural practices and the surrounding climatic conditions. Flesh color. — Considered medium orange (RHS Orange 25 A to RHS Orange 25 B).

Stone:

*Stone cavity*.—Color. — The stone cavity shows the same orange color as the flesh color (RHS Orange 25 A to RHS Orange 25 B). Length. — Approximately 28.0 to 31.0 millimeters.

*Stone type*.—Free, but the stone seems to be slightly attached to the flesh through its base.

*Size*.—Considered medium for the variety. The stone size varies depending upon the tree vigor, crop load and prevailing growing conditions. Length. — Approximately 24.0 to 26.0 millimeters. Width. — Approximately 18.0 to 20.0 millimeters. Diameter. — Approximately 10.0 to 11.0 millimeters.

*Stone form*.—Ovoid.

*Stone form* (*viewed from stem end*).—Ovate flattened.

*Stone form* (*lateral view*).—Oblong.

*Stone base shape*.—Round to slightly concave.

*Stone apex shape*.—Slightly pointed.

*Symmetry*.—No symmetry is observed.

*Stone surface*.—Surface texture. — Slightly rough. Ridges at stone surface. — The ridges are present on both sides of the stone. A ridge is generally narrow. The ridges begin at the base and are extending all along the stone length.

*Stone color*.—The color of the dry stone is generally considered a greyed orange (RHS Greyed Orange N 167 A).

*Tendency to split*.—Splitting is absent.

*Kernel*.—Taste. — Bitter. Size. — Medium. Length. — Approximately 18.0 millimeters. Width. — Approximately 12.0 millimeters. Thickness. — Approximately 7.0 millimeters. Form. — Ovate. Color. — The kernel skin is a greyed orange (RHS Greyed Orange 164 B or RHS Greyed Orange 165 C). The almond, which is the seed of the kernel, is considered white (RHS White 155 A to RHS White 155 B).

*Use*.—The subject variety 'APRIREVE' is considered to be a apricot tree with a semi early season maturity, and which produces fruits that are considered firm, attractively and luminously colored. Fruits have a balanced taste between acidity and sugar. They are excellent for uncooked or cooked consumption, melting and juicy when at full maturity. Fruits have excellent gustative qualities and are very aromatic. They are also useful for both local markets and very long distance shipping.

*Keeping quality*.—Good. Fruits are well preserved during at least 3 weeks after harvest in a cold atmosphere. Fruits are considered to have a long shelf life after harvesting without alteration.

*Shipping quality*.—Considered good. The fruits of the new apricot variety showed very little skin scarring or flesh bruises in picking, packing and shipping trials.

*Resistance to insects and disease*.—No particular susceptibilities were noted. Under meticulous observations during planting, growing and harvesting of fruits, no particular resistance or sensitivity to plant or fruits diseases were noticed. Any variety, observed during indexing of plant characteristics, with abnormal fungus, bacterial virus or insect sensitivity is destroyed and eliminated from our breeding program. Although the new variety of apricot tree possesses the described characteristics when grown under the ecological conditions prevailing near Elne, Pyrénées-Orienteles departement, France, it should be understood that variations of the usual magnitude and characteristics incident to changes in growing conditions, fertilization, pruning, pest control and horticultural management are to be expected.

We claim:

1. A new and distinct variety of apricot tree as illustrated and described, characterized by its self-fertility and no susceptibility to pests and diseases and by fruits of very good firmness, of very long shelf life without alteration after harvesting, and with an orange flesh of high eating quality, aromatic and with a high level of sugar, and with an attractive luminous orange red skin on a yellow orange background.

* * * * *